(12) United States Patent
Nishimura et al.

(10) Patent No.: US 6,831,195 B2
(45) Date of Patent: Dec. 14, 2004

(54) METHOD FOR PRODUCTION OF ORGANIC ACID

(75) Inventors: Takeshi Nishimura, Himeji (JP); Tetsuji Mitsumoto, Himeji (JP); Kazuhiko Sakamoto, Himeji (JP); Hidefumi Haramaki, Himeji (JP)

(73) Assignee: Nippon Shokubai, Co., LTD, Osaka (JP)

( * ) Notice: Subject to any disclaimer, the term of this patent is extended or adjusted under 35 U.S.C. 154(b) by 105 days.

(21) Appl. No.: 10/224,677

(22) Filed: Aug. 21, 2002

(65) Prior Publication Data

US 2003/0045749 A1 Mar. 6, 2003

(30) Foreign Application Priority Data

Sep. 3, 2001 (JP) ......................... 2001-266189

(51) Int. Cl.⁷ .............................. C07C 27/10
(52) U.S. Cl. .................. 562/512.2; 562/407; 562/523; 560/77; 560/131; 560/208; 560/241.1
(58) Field of Search ................. 562/400, 405, 562/512, 606, 598; 560/1, 128, 129

(56) References Cited

U.S. PATENT DOCUMENTS 4,954,650 A * 9/1990 Abe et al. ................... 562/534
5,334,755 A * 8/1994 Yoneda et al. ............... 562/519

FOREIGN PATENT DOCUMENTS

JP          A-49-73381          11/1972

* cited by examiner

Primary Examiner—Johann Richter
Assistant Examiner—Karl Puttlitz
(74) Attorney, Agent, or Firm—Mathews, Collins, Shepherd & McKay, P.A.

(57) ABSTRACT

A method for producing an organic acid and/or an organic acid ester which utilizes a steam system permitting stable production of an organic acid and/or an organic acid ester and realizing a high thermal efficiency constantly relative to the waste heat generated in the process of the production is provided. More particularly, this invention concerns a method for the production of an organic acid and/or an organic acid ester, wherein heat generated in the process for producing an organic acid and/or an organic acid ester is recovered in the form of steam, and the steam is used in any of the following forms: ① thermal energy, ② dynamic energy, and ③ electrical energy in the process for producing an organic acid and/or an organic acid ester.

9 Claims, 2 Drawing Sheets

METHOD FOR PRODUCTION OF ORGANIC ACID

BACKGROUND OF THE INVENTION

1. Field of the Invention

This invention relates to a novel method for the production of an organic acid and/or an organic acid ester. More particularly, this invention relates to a method for the production of an organic acid and/or an organic acid ester, with the thermal efficiency and consequently the operational efficiency thereof enhanced by effectively utilizing the large volume of heat generated in the process of production of an organic acid and/or an organic acid ester.

2. Description of the Related Art

Since large commercial plants such as chemical plants emit waste heat in large volumes, efforts have been devoted to make effective use of the waste heat to the fullest possible extent by introducing a technique for the utilization of heat.

The process for producing acrylic acid by the reaction of catalytic gas phase oxidation also emits waste heat in a large volume. Thus, efforts have been directed toward realizing effective use of the waste heat to the fullest possible extent by introducing a technique for the utilization of heat.

In performing this reaction of catalytic gas phase oxidation, since the raw material therefor must be supplied in a gaseous form, the liquefied propylene adopted as the raw material is gasified through a vaporizer and then supplied to a reactor. When the raw material is subjected to catalytic gas phase oxidation using a molecular oxygen-containing gas in the presence of a catalyst, a gaseous product which contains an organic acid aimed at by the reaction and by-products is obtained. The reaction generates the heat of reaction in a large volume at the same time. Generally, this heat of reaction is recovered by means of a heat exchanger. Meanwhile, the gas obtained by the catalytic gas phase oxidation is led to an organic acid absorbing column for the purpose of allowing the produced organic acid to be isolated, and exposed to an absorbing solvent (generally, water) so as to be cooled. And the organic acid and by-products are absorbed in the solvent. In a solvent separating column, this solution is deprived of the solvent contained therein. Then, in a purifying column, the resultant solution is distilled to separate the purified organic acid.

As regards the utilization of the heat of reaction that is generated when the organic acid is produced by means of the reaction of catalytic gas phase oxidation, JP-A-49-73381, for example, proposes a method for the recovery of the heat of reaction. This method of recovering the heat of reaction is embodied in the production of acrolein by the catalytic gas phase oxidation of propylene or the production of phthalic anhydride by the catalytic gas phase oxidation of ortho-xylene or naphthalene and is characterized by utilizing part of the heat of reaction generated for inducing generation of steam and superheating the produced steam with the remainder of the heat of reaction. According to this method, the heat of reaction generated by the reaction is utilized for the generation of steam and then utilized for the production of superheated steam. The superheated steam obtained is used as the source of motive power for a steam turbine which is connected to a compressor serving to supply air as the raw material for the reaction of catalytic gas phase oxidation. This method permits the heat of reaction to be recovered for reuse highly advantageously in terms of economy and operational efficiency.

The invention disclosed in the patent publication mentioned above, however, is a method for the recovery of the heat that emanates from the single-stage reaction of catalytic gas phase oxidation. When it is applied to an actual commercial-scale production plant, it occasionally requires promoting the reaction by disposing a plurality of reactors in series or in parallel and operating them so as to perform the necessary treatment in a series or parallel pattern. In this case, the method for the recovery of the heat of reaction mentioned above is required to be applied to each of the plurality of reactors. Therefore, the devices used for the recovery of the heat of reaction are required to be in such a quantity as to be commensurate with the number of reactors to be disposed. These requirements add to the cost of equipment and the measure for security and the measure for environmental protection which are brought about by the complication and exaction of the configuration of equipment. Thus, the invention has incurred the problem of augmenting the cost of design and development and the running cost as well.

The object of this invention is to provide a method for the production of an organic acid and/or an organic acid ester which comprises utilizing a steam system capable of constantly performing a reaction of catalytic gas phase oxidation without reference to the form of the reaction of an organic acid and capable of constantly realizing a high thermal efficiency for the waste heat generated in the process of production in any form of the reaction. As concrete examples of reaction of the organic acid, (1) one-stage reaction of catalytic gas phase oxidation or a multiple-stage reaction of catalytic gas phase oxidation; and (2) the mass production using a plurality of reactors disposed in a series or parallel arrangement and operated to perform the treatment in a series or parallel pattern or the treatment by the use of one reactor which is equipped with one or a plurality of chambers may be cited. Particularly the multiple-stage reaction of catalytic gas phase oxidation is implemented in various forms such as the treatment by using one or a plurality of reactors for each of the reactions and one reactor with intermediate tube sheets into a plurality of chambers and circulating a heat transfer media to each of the chambers independently so as to allow different reactions to proceed in the different chambers.

SUMMARY OF THE INVENTION

The present inventors have carried out diligent studies repeatedly. They have consequently found that, by recovering the heat generated at various places in the process for the production of an organic acid and/or an organic acid ester in the form of steam by a heat generating device and further using effectively the recovered steam at various places in the process for the production of an organic acid and/or an organic acid ester, it is made possible to perform stably the reaction of catalytic gas phase oxidation constantly and realize a steam system of constantly high thermal efficiency operated by the use of the waste heat generated in the process in any forms of reaction. The present inventors, regarding the system for controlling the device for the generation of steam and the steam line, have further found that, by controlling the pressure in the device and in the line independently, it is made possible to recover the energy retained by the generated heat more effectively in the form of steam throughout the whole process and use it stably even when the multiple-stage reaction of catalytic gas phase oxidation uses the heat transfer media at temperatures varied for the individual component reactions.

The method contemplated by this invention for the production of an organic acid and/or an organic acid ester is characterized by recovering the heat generated in the process for the production of an organic acid and/or an organic acid ester in the form of steam and using the steam formed in the process for the production of an organic acid and/or an organic acid ester in any forms of ① thermal energy, ② mechanical energy, and ③ electric energy. When the method of this invention is used, the by-products and the discharged heat arising from the production plant can be utilized highly effectively as in simplifying the system and decreasing the quantity of the discharged steam. Particularly when (1) devices for generating steam and (2) steam lines for connecting the devices for generating steam to devices for consuming the steam are independently subjected to control of pressure with a view to recovering the heat in the form of steam and using the steam in a complex manner at various places in the process of production, the control can be implemented so that the steams of varying pressures individually obtained in the devices for generating steam may be individually supplied to the devices for consuming the steam under pressures proper therefor through the steam lines of varying pressures. Thus, the effects of the present invention can be augmented further.

DETAILED DESCRIPTION OF THE INVENTION

The above and other objects, features, and advantages of the present invention will become clear from the following description of the preferred embodiments.

The method of this invention for the production of an organic acid and/or an organic acid ester is characterized by recovering the heat generated in the process for the production of an organic acid and/or an organic acid ester in the form of steam and using the steam thus formed in the process for the production of an organic acid and/or an organic acid ester in any forms of ① thermal energy, ② mechanical energy, and ③ electric energy. It is preferably characterized by recovering the heat generated in the process for the production of an organic acid and/or an organic acid ester in the form of steam and, while steam generating devices and steam lines are independently subjected to control of pressure, using the steam in the process for the production of an organic acid and/or an organic acid ester.

While steam is not in short supply, therefore, the method does not need to introduce steam into the production plant through a steam line from an external source. Further, the steam generated is not only withdrawn simple as the source of power but also effectively utilized within the production plant (consumption of its own). Thus, the method excels in the efficiency of recovering the heat generated, contributes to the reduction of production cost, and accomplishes simplification of the steam system and reduction of the purged steam. Incidentally, this invention requires the generated steam mentioned above to be usable in the process for the production of an organic acid and/or an organic acid ester and imposes no restriction whatever on the use of the steam for any other purpose.

Now, preferred embodiment of this invention will be described below with reference to the accompanying diagrams.

Figure 1:
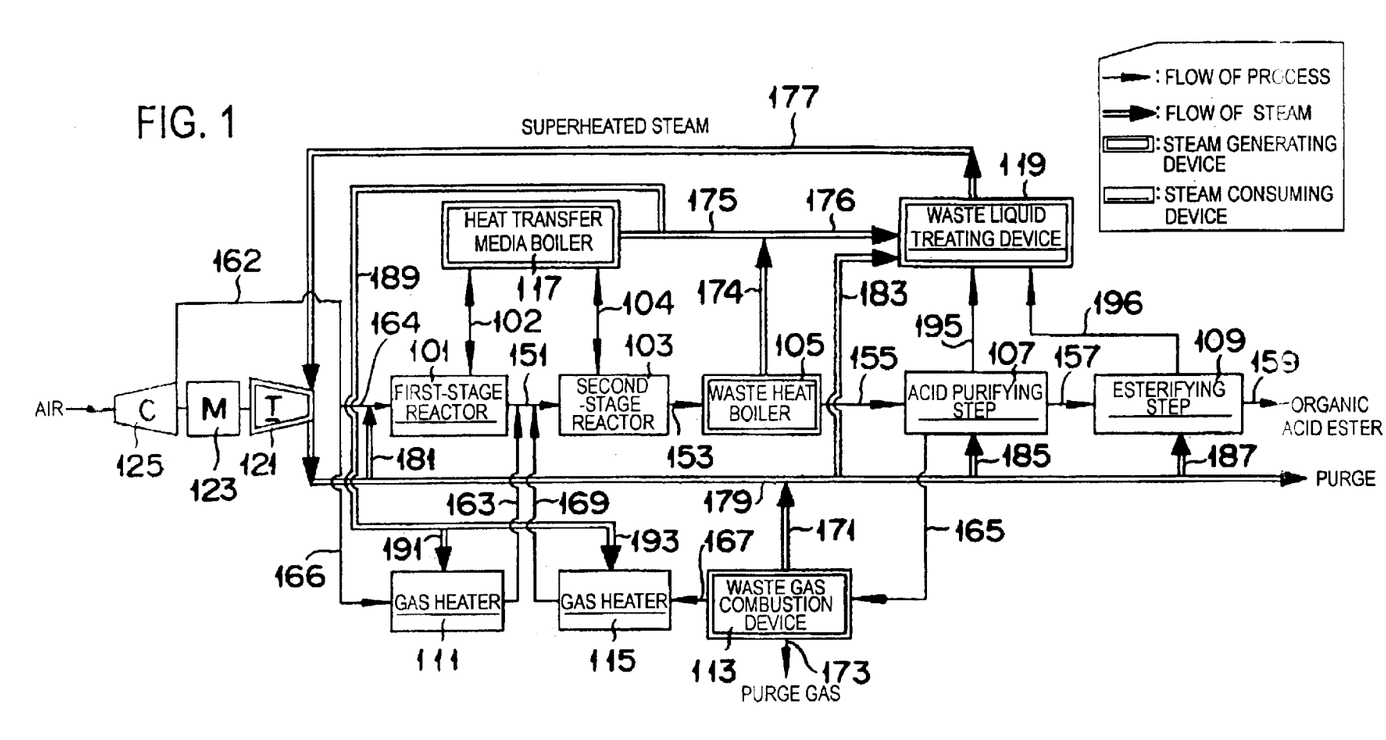
FIG. 1 is a schematic diagram of the process for the production of an organic acid and/or an organic acid ester and the steam system (partly expressed as "a step") which are used in one preferred embodiment of the method of this invention for the production of an organic acid and/or an organic acid ester.

FIG. 1 is a schematic diagram of the main process for the production of an organic acid and/or an organic acid ester and the steam system (partly expressed as "a step") which are used in one preferred embodiment of the method of this invention for the production of an organic acid and/or an organic acid ester. In this diagram, the flow of the production process is indicated with single-line arrow marks (→) and the devices or the steps used in this process are indicated each with a single-line frame. The flow of steam is indicated with double-line arrow marks (⇒) and the devices or the steps used for this flow are indicated each with a double-line frame. In these devices or steps, those devices or steps for the consumption of the generated steam are identified by having their designations underlined.

As regards the flow of the process for production of an organic acid and/or an organic acid ester in the embodiment illustrated in FIG. 1, first a preheated raw material gas, an oxygen-containing gas, and steam are mixed and the resultant mixture is supplied to a first-stage reactor 101 and subjected therein to a first-stage reaction of catalytic gas phase oxidation. The gas formed by this reaction is forwarded through a line 151 directly to a second-stage reactor 103 and subjected therein to a second-stage reaction of catalytic gas phase oxidation so as to produce a target organic acid.

The first-stage reactor 101 and the second-stage reactor 103 are both those of the shell-and-tube type. They effect the reaction of catalytic gas phase oxidation by supplying a raw material gas through a raw material supplying line to the catalyst packed in one or more reaction tubes (tube bundle) disposed inside the shell of the reactor. The raw material gas formed by mixing the raw material for the reaction with an oxygen-containing gas and others is supplied, for example, through a raw material gas supplying nozzle into the reaction tubes packed with the catalyst, oxidized in the reaction tubes and converted into a reaction product. Then, the reaction product is discharged as a formed gas through a reaction gas outlet nozzle.

Thereafter, this formed gas is forwarded to an acid purifying step 107 through a line 153, a waste heat boiler 105 which is one of the steam generating devices, and a line 155 and caused by an operation which will be specifically described below to form a purified organic acid. This purified organic acid is forwarded to an esterifying step 109 through a line 157 and caused by an operation which will be specifically described below to form a purified organic acid ester, which is withdrawn through a line 159. The esterifying step 109 mentioned above embraces a step for purifying the organic acid ester.

Figure 2:
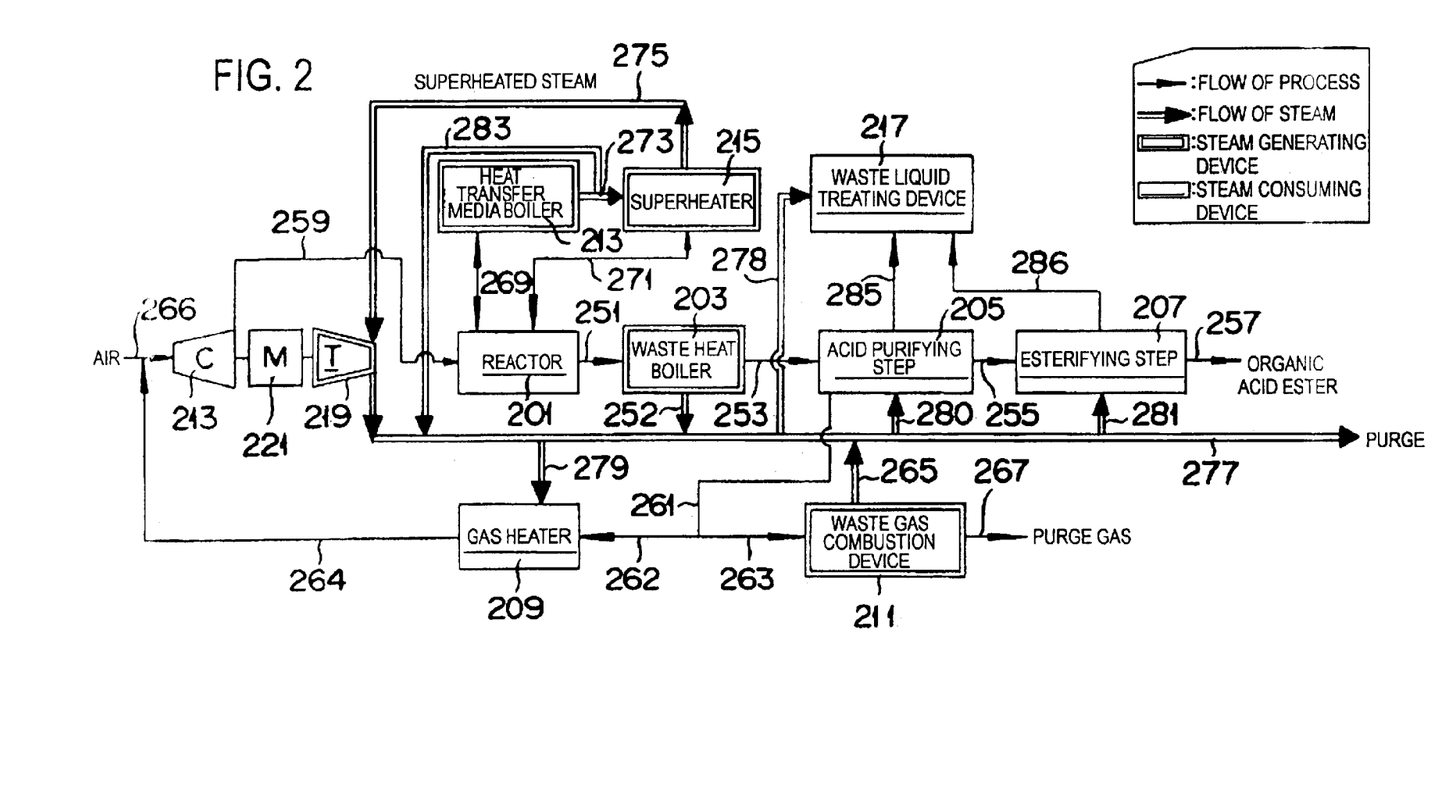
FIG. 2 is a schematic diagram of the process for the production of an organic acid and/or an organic acid ester and the steam system (partly expressed as "a step") which are used in another preferred embodiment of the method of this invention for the production of an organic acid and/or an organic acid ester, specifically in implementing a two-stage catalytic gas phase oxidation with one reactor.

The term "acid purifying step" as used herein refers to the part of operation which includes and follows the step for absorbing the organic acid (providing that the esterifying step is excluded). That is, the acid purifying step comprises an organic acid absorbing column, a column for separating an organic acid from an aqueous organic acid solution and purifying the separated organic acid, an intermediate storage tank, and a storage tank for a purified organic acid and embraces a distilling column, an extractor, and a heat exchanger which are necessary for the separation and purification. The acid purifying step in the embodiment illustrated in FIG. 2 is similarly defined.

At the absorbing step within the acid purifying step 107, the formed gas which has passed through the waste heat boiler 105 is advanced through the line 155 to the organic acid absorbing column and exposed therein to a solvent, generally water, and collected as an aqueous organic acid solution. The aqueous organic acid solution is forwarded to the acid purifying device in the acid purifying step 107.

At the acid purifying step 107, the aqueous organic acid solution forwarded from the absorbing step is extracted in the extractor and/or rectified in the distilling column to obtain an organic acid aimed at. The wasted liquid which consequently occurs is forwarded to a waste liquid treating device 119. The separated organic acid-containing component resulting from the extraction is subsequently separated by distillation from a light component and a heavy component and, as a result, enabled to obtain a purified organic acid. The acid purifying step 107 in the embodiment of FIG. 2 performs the same treatment.

At the esterifying step 109, the organic acid produced at the acid purifying step 107 is caused to react with an alcohol and allowed to be esterified. The reaction product is separated by the operation of distillation and/or extraction into an unaltered organic acid and the alcohol on one part and an organic acid ester on the other part. Subsequently, it is separated by distillation from a light component and a heavy component and, as a result, enabled to obtain a purified organic acid ester.

The esterifying step comprises a column for esterifying the purified organic acid emanating from the acid purifying step by reaction with an alcohol, a column for separating and purifying the resultant organic acid ester, an intermediate storage tank, and a storage tank for the purified organic acid ester and embraces an esterifying reactor, a distilling column, an extractor, and heat exchanger which are necessary for the esterification, separation, and purification. The esterifying step in the embodiment of FIG. 2 is defined similarly.

The waste gas which occurs when the aqueous organic acid solution is collected and separated at the absorbing step mentioned above is forwarded through a line 165 to a waste gas combustion device 113, subjected therein to a combustion treatment, and purged as a treated gas from the system via a line 173.

Part of the gas resulting from the combustion treatment is forwarded from the waste gas combustion device 113 via a line 167 to a gas heater 115, preheated to a prescribed temperature (generally, a temperature not lower than the dew point), then returned via a line 169 to the line 151, mixed therein with the formed gas flowing therethrough, and recycled to the second-stage reactor 103.

The oxygen-containing gas which is supplied to the second-stage reactor 103 is compressed by an oxygen-containing gas supplying device, further heated by a gas heater 111 to a temperature suitable for the second-stage reaction of catalytic gas phase oxidation, then forwarded via a line 163 to the line 151, mixed therein with the formed gas flowing therethrough, and supplied to the second-stage reactor 103. As the oxygen-containing gas supplying device, such a compressor 125 may be utilized. The oxygen-containing gas supplying device is preferred to be provided with a steam turbine 121 utilizing the superheated steam as the drive source.

As the gas heaters 111 and 115, fin type heat exchangers, for example, may be used. In the shell of the gas heater utilizing a fin type heat exchanger, finned heat transfer tubes are laid out. In order that the heat transfer tubes may permit passage of steam therein as the intra-tube fluid, the finned heat transfer tubes are connected at one terminal side to a steam introducing part and at the other terminal side to a steam discharging part. Further, for the purpose of enabling the oxygen-containing gas to be supplied through a line as the extra-tube fluid (the shell side fluid) for the gas heater, the interior of the shell of the gas heater is provided at one terminal thereof with an oxygen-containing gas inlet nozzle and at the other terminal thereof with an oxygen-containing gas outlet nozzle. Incidentally, the gas heaters 111 and 115 do not need to be limited to fin type heat exchangers. Optionally, plate-type heat exchangers and shell-and-tube heat exchangers may be utilized instead.

The present embodiment is furnished with a steam system for recovering the heat generated in the process of production and using the recovered heat. In the steam system of this type, the generated heat is recovered in the form of steam and the produced steam is used at the step for the production of an organic acid and/or an organic acid ester.

In the present embodiment, by independently controlling the pressure of the steam generating device and the pressure of the steam line, it is made possible to operate the plant more stably.

The term "generated heat" as used herein is construed as embracing (1) the heat of reaction and (2) the heat generated by the combustion of the gas formed by the reaction and the waste liquid (arising at the step for purification).

Of the generated heat, (1) the heat of reaction mentioned above means the heat which is generated within the reactor. The term "reactor" as used herein not only means the reactor to be used in the production of an organic acid but also embraces the esterifying reactor to be used in the production of an organic acid ester. In the present embodiment, the first-stage through second-stage reactors which are used for the production of an organic acid are mainly meant by the term. When the production relies on a plurality of reactors, the term embraces all the reactors involved. The recovery of the heat of reaction, in the present embodiment, is mainly carried out with a heat transfer media in the first-stage and the second-stage reactors which are used for the production of an organic acid. Then, by using the heat of reaction deprived by the heat transfer media, the heat transfer media boiler is enabled to generate steam and recover the generated steam. Since the heat of reaction is more or less taken out besides toward the gas formed by the reaction, the waste heat boiler disposed subsequently to the second-stage reactor is enabled by using this heat of reaction to generate and recover steam.

The expression "the heat of combustion of the gas formed by the reaction" of the item (2) refers to the heat which is generated when the waste gas emanating during the collection of the gas formed by the reaction at the absorbing step is subjected to a treatment of combustion, optionally having the efficiency of combustion thereof exalted by addition of an auxiliary fuel. This heat of combustion is recovered by subjecting the waste gas to combustion in the waste gas combustion device and consequently inducing generation of steam.

The reaction of catalytic gas phase oxidation forms water and other by-products. The water and such by-products are separated and discharged respectively as waste water and waste oil. The heat of combustion of the waste liquid of the item (2) refers to the heat which is generated when the waste water and the waste oil are subjected simultaneously or independently to a treatment of combustion. This heat of combustion of the waste liquid is recovered by subjecting the waste liquid to combustion in the waste liquid combustion unit of the waste liquid treating device and consequently inducing generation of steam.

Incidentally, the gas formed by the reaction of the item (2) and the relevant waste liquid may be collectively burnt in one waste gas and waste liquid treating device. The heat of combustion generated in this case contains both the heat of combustion of the gas formed by the reaction and the heat of combustion of the waste liquid.

Now, the steam system mentioned above in the present embodiment will be described below with reference to FIG. 1.

First, the heat transfer media which fill the shells of the first-stage reactor 101 and the second-stage reactor 103 are both circulated as with a circulating pump respectively through lines 102 and 104 to a heat transfer media boiler 117. Consequently, in the reaction of catalytic gas phase oxidation using heat transfer media of different temperatures in the reactors 101 and 103, the heats of reaction generated in the reactors 101 and 103 are recovered in the one heat transfer media boiler 117 in the form of steam.

Here, the reactor 101 and the reactor 103 use heat transfer media of different temperatures because different reactions are proceeding in the reactor 101 and the reactor 103 and, in order for these reactors to retain their respectively different reaction temperatures at the respectively fixed levels, the temperatures of the heat transfer media being circulated within the reactors need to be respectively adjusted. Since the heats of reaction generated in the reactors therefore differ, the temperatures of heat transfer media which are circulated to the heat transfer media boiler 117 are different. The heat transfer media in the heat transfer media boiler 117 are adjusted to different temperatures by means of heat exchange and then returned again to the relevant reactors.

The heat transfer media boiler 117 that recovers the heat of reaction is preferred to generate steam at as high a pressure as possible. When one heat transfer media boiler 117 is used for recovering the heat of reaction, the steam system can be simplified, the thermal efficiency exalted, and the volume of the steam suffered to escape the recovery decreased as compared with the use of different heat transfer media boilers for a heat transfer media of a high temperature and a heat transfer media of a low temperature. It is naturally permissible to install heat transfer media boilers as apportioned to reactors or to reaction temperatures and operate them to recover steams of respectively proper temperatures.

Incidentally, the boilers which can be used herein include such general shell-and-tube type heat exchangers as kettle type heat exchangers which pass a heat transfer media on the tube side and generate steam on the shell side and natural circulation type heat exchangers which pass a heat transfer media on the shell side and generate steam on the tube side, for example. As the heat transfer media, organic heat transfer media such as potassium nitrate-sodium nitrite-sodium nitrate mixture, potassium nitrate-sodium nitrite mixture, Dowtherm, and Therm-S may be used, for example.

In the heat transfer media boiler 117 which is a steam generating device, generally saturated steam is generated. The steam pressure may be freely selected so long as it is higher than the steam pressure equivalent to the solidifying point of the heat transfer media and lower than the steam pressure equivalent to the temperature of the heat transfer media. In the sense of effectively using the generated steam, the steam pressure is in the range of 0.5–5.0 MPa gauge, preferably in the range of 1.0–4.8 MPa gauge, and more preferably in the range of 1.5–4.5 MPa gauge. If the operating pressure is low, the heat transfer media will not only approximate closely to the solidifying point and tend to solidify but also increase viscosity and degrade the efficiency of heat transfer. Fully satisfactory recovery of heat, therefore, requires the equipment to be enlarged. Conversely, if the operating pressure is unduly heightened, the design pressure will rise and consequently boost the cost of the equipment. Further, since the enthalpy of steam is not varied very much at a high pressure, an increase of the pressure of the generated steam will not vary appreciably the amount of the steam to be generated.

The means to control the pressure in the heat transfer media boiler 117 does not need to be particularly restricted. It may be a valve (control valve), for example.

The pressure inside the heat transfer media boiler 117 may be measured with pressure gauges of the Bourdon tube type or the diaphragm type or pressure sensors disposed at proper places in the heat transfer media boiler 117.

The temperature inside the steam generating device may be measured with thermoelectric thermometers, resistance thermometers, and expansion thermometers disposed at proper places in lines or devices.

A control part which is capable of automatically controlling the pressure may be assembled by using the detecting units of the pressure gauge and the thermometer and the operating units of the pressure controlling valve.

Since the pressure controlling means, the pressure temperature and measuring means, or the like in the steam generating device are identical with those of the steam generating device other than the heat transfer media boiler and with those of the steam generating device of the embodiment of FIG. 2, these means in the other steam generating device and in the steam generating device of the embodiment of FIG. 2 will be omitted from the following description to avoid repetition.

Part of the steam generated in the heat transfer media boiler 117 is forwarded through steam lines 175, 176 to a waste liquid treating device 119.

The pressure of the steam of the steam line 175 is controlled so as to equal to or to be 0.05–0.1 MPa lower than the pressure in the heat transfer media boiler.

The control of the pressure of the steam line 175 is carried out independently on the control of the pressure on the side of the heat transfer media boiler 117 so as to advance the flow of the pressure as far as the waste liquid treating device 119 while repressing the loss of the flow through the steam line to the smallest possible extent. Further, for the purpose of repressing the loss of the thermal energy and the loss of the pressure both of the steam in the steam line to the smallest possible extents, it is commendable to keep the steam line covered with a heat insulator or avoid inserting a sharp corner part into the line anywhere in the entire length thereof, for example. It is also permissible to limit the control of pressure to the line and omit controlling the pressure of the heat transfer media boiler.

Incidentally, the measurement and control of the pressure and temperature in the steam line in the present embodiment and in the embodiment of FIG. 2 is identical with that effected in the steam generating device mentioned above.

The formed gas obtained in the second-stage reactor 103 is forwarded through the line 153 to the waste heat boiler 105. The generated heat entrained by the formed gas is utilized as the heat source for the waste heat boiler 105 to generate steam and recover residual heat.

The temperature of the steam in the waste heat boiler 105 is only required to be capable of preventing the boiler and the line from being clogged. The waste heat boiler 105 passes the formed gas itself obtained in the second-stage reactor 103 and effectively recovers the heat of reaction which is brought out toward the formed gas side. The organic acid-containing gas, however, contains an easily occluding substance. If the temperature of the formed gas is unduly lowered by means of heat exchange in the waste heat boiler 105, the easily occluding substance will be precipitated to induce the problem of occlusion and render the operation of the production process no longer practicable. In the waste heat boiler 105, therefore, the temperature of the generated steam is controlled to a level which is capable of preventing the boiler and the line from being clogged. The temperature of the steam generated in the waste heat boiler 105 is variable with the kind of process. Preferably, the temperature and pressure of the steam is so controlled that the temperature of the organic acid gas may be retained above 140° C. in the case of acrylic acid or above 230° C. in the case of methacrylic acid.

The steam generated in the waste heat boiler 105 is forwarded through a steam line 174 and further through the steam line 176 to the waste liquid treating device 119. Since the steam line 174 joins the steam line 176 further front than the waste liquid treating device 119, the pressure of the generated steam in the steam line 174 is a level on a par with the pressure in the heat transfer media boiler 117.

It is further permissible to interpose a waste heat boiler between the first-stage reactor and the second-stage reactor, cool the outlet gas of the first-stage reactor to a level optimum for supply to the second-stage reactor, and consequently recover the heat of the outlet gas. When acrylic acid or methacrylic acid is produced by the reaction of a two-stage catalytic gas phase oxidation, acrolein or methacrolein is respectively formed in the first-stage reactor. The recovery of the heat is effective in precluding this reaction of autoxidation.

In the waste liquid treating device 119, the waste liquids brought in from the acid purifying step 107 and the esterifying step 109 respectively through a line 195 and a line 196 are subjected to a treatment of combustion optionally after incorporation therein of a combustion auxiliary (auxiliary fuel) with a view to acquiring the optimum efficiency of combustion. By utilizing the heat of combustion, the steam brought in through the steam line 176 is superheated to induce generation of superheated steam. Incidentally, in the waste liquid treating device, the waste water and/or the waste oil emanating from the acid purifying step 107 and the waste water and/or the waste oil emanating from the esterifying step 109 are treated either simultaneously or separately of each other.

The pressure in the waste liquid combustion device (concurrently serving as a superheated steam generating device) of the steam recovering part in the waste liquid treating device 119 is lower than the pressure of the heat transfer media boiler. The temperature of superheating of the steam is in the range of 20–150° C., preferably in the range of 40–130° C., and more preferably in the range of 50–120° C. because the superheated steam is used in a turbine. As concrete examples of the water liquid combustion device, submerged combustion furnaces and dry combustion furnaces may be cited.

The combustion temperature of the waste liquid in the waste liquid treating device 119 depends on the question whether or not a combustion auxiliary is used. The upper limit of this temperature is set at about 1200° C. in consideration of such factors as the melting of dust and the generation of $NO_x$ and the lower limit thereof is set at 900° C. from the viewpoint of ensuring perfect combustion of organic substances and preventing emission of offensive odor. The combustion optionally uses a combustion auxiliary. The temperature for the heat recovery from the combustion gas is decided on the basis of the concentrations of sulfur components contained in the waste oil and the combustion auxiliary lest the equipment should be corroded with sulfuric acid.

Meanwhile, part of the steam generated in the heat transfer media boiler 117 is forwarded through steam lines 189, 191 which are branched from the steam line 175 to the gas heater 111 and made therein to exchange heat with the compressed air brought in by an oxygen-containing gas supplying device through a line 162 and further through a line 166 and consequently spent in heating the compressed air to a prescribed temperature. Incidentally, the oxygen-containing gas supplying device is provided with a compressor 125, a motor 123, and the steam turbine 121.

Likewise, part of the steam generated in the heat transfer media boiler 117 is forwarded through the steam line 189 and a steam line 193 which are branched from the steam line 175 to the gas heater 115 and made therein to exchange heat with a recycle gas brought in from the waste gas combustion device 113 through the line 167 and consequently spent in heating the unaltered gas to a prescribed temperature.

A compressor not illustrated in the diagram is also used when the recycle gas is circulated via the gas heater 115 to the second-stage reactor 103. It may be provided with a steam turbine and enabled by utilizing superheated steam to recover power and low-pressure steam in the same manner.

The pressures in the steam lines 189, 191, and 193 do not need to be particularly controlled. The gas heater is only required to be designed and used to permit effective utilization of the energy of the steam which is generated in the heat transfer media boiler. Naturally, it may be furnished with a pressure-reducing valve, as occasion demands, so as to optimize the pressure and the temperature of the steam. When these steam lines are still deficient in pressure and temperature, part of the superheated steam of high temperature and high pressure obtained in the waste liquid treating device 119 may be supplied to the steam lines.

As concerns the distribution of the steam generated in the heat transfer media boiler 117, it suffices to decide the ratio of apportions of the steam to the waste liquid treating device 119, the gas heater 111, and the gas heater 115 by taking into account the thermal energy balance of the whole production plant.

The superheated steam generated in the waste liquid treating device 119 is forwarded through the steam line 177 to the steam turbine 121 in the oxygen-containing gas supplying device and spent therein for the purpose of converting the thermal energy entrained by the superheated steam of high temperature and high pressure into a useful dynamic energy (mechanical work).

In the steam turbine 121, the superheated steam of high temperature and high pressure is passed through the nozzles in the turbine and consequently made to undergo adiabatic expansion and give rise to a high-speed steam current and this high-speed steam current is utilized for driving the rotary vanes of the turbine 121 and enabling them to do a mechanical work.

In the present embodiment, a extraction turbine or a back-pressure turbine may be used as the steam turbine for effecting secondary utilization of the superheated steam used in the steam turbine 121 and heightening the thermal efficiency of the superheated steam. It is conceivable to connect an electric generator to the steam turbine, convert the thermal energy to an electric energy, and utilize the electric energy as the power source necessary for the production plant.

The exhaust steam which still retains a useful thermal energy remains after the superheated steam has been used as the dynamic energy in the steam turbine 121. In the present embodiment, therefore, the effective utilization of energy is attained by complex utilization and multiple-stage utilization of the useful thermal energy retained by the exhaust steam. To be specific, the useful thermal energy is used as the power source and the heat source for various devices (steam consuming devices) in the production plant through the medium of the steam line 179 which serves as the mainstay and is utilized as effectively as possible by means of heat exchange or the like. In the light of the importance of the, optimum distribution of exhaust steam, it is advantageous to strive to ensure supply of steam of a pressure proper for a given steam consuming device in the production plant as by apportioning preferentially a steam of a high pressure and a high temperature to such devices and instruments as necessitate a steam of comparatively high temperature and apportioning a steam of a lowered pressure and a lowered temperature to heat exchangers or the like which operate satisfactorily with of a steam of a comparatively low temperature.

The exhaust steam is supplied as the steam for application to the reaction of catalytic gas phase oxidation through a steam line 179 and further through a steam line 181 to a line 164, mixed therein with the raw material gas, and then supplied to and used in the first-stage reactor 101. The reason for this is that the reaction itself needs the steam. In the method for producing acrylic acid, for example, the raw material gas such as propylene is catalytically oxidized under the conditions of gas phase and high temperature in the presence of an oxygen-containing gas and steam; the propylene being converted into acrolein by the first-stage reaction of oxidation and the acrolein being converted into acrylic acid by the second-stage reaction of oxidation.

The pressure of the steam line 179, owing to not only the supply of steam from the steam turbine 121 but also the supply of steam from other steam generating devices, is prone to changes in the flow rate of steam and in the amount of energy entrained by the steam as the supply and the circulation of steam to the relevant steam consuming devices are continued. From this fact, it is inferred that the line does not need to be wholly retained under the same pressure but that the pressure control has only to be so performed as to retain each part of the relevant steam line under the optimum pressure. Thus, the pressure of the steam line 179 cannot be uniquely defined but is controlled generally in the range of 0.1–2 MPa gauge and preferably in the range of 0.25–1 MPa gauge. In the process in which the steam from the steam line 179 is used in the relevant steam consuming devices and is then purged from the system, the energy entrained by the steam is consumed to the maximum extent. What is so purged does not need to be steam but may have reverted to water.

The exhaust steam, when supplied through the steam line 179 and further through a steam line 183 to the waste liquid treating device 119 which serves the purpose of treating the waste liquid by combustion, is utilized in the waste liquid heating heat exchanger for the purpose of heating the waste liquid to the prescribed temperature. The reason for utilizing the steam for the heat exchanger is that, for the sake of treating by combustion the waste water and/or the waste oil separated at the acid purifying step 107 and the esterifying step 109, the preparatory elevation of the temperature is advantageous in repressing to the minimum the consumption of the combustion auxiliary which is an external energy source necessary for the combustion.

In the present embodiment, the waste water and the waste oil are treated either simultaneously or independently of each other in the waste liquid treating device 119. At this time, the treatment by combustion is carried out by the method of direct combustion (1) in the presence of the combustion auxiliary when the waste liquid to be treated happens to be a waste water containing an organic substance at a low concentration, (2) not particularly in the presence of the combustion auxiliary when the waste liquid happens to be a waste oil containing an organic substance at a high concentration, or (3) in the presence of the combustion auxiliary in an amount proper for the concentration of an organic substance contained in the waste liquid when the waste water and the waste oil is treated together. While the conventional treatment by combustion of the waste water has required the use of a combustion auxiliary in a large quantity, the utilization of part of the steam generated in the plant for the production of an organic acid for elevating the temperature of the waste water permits a generous reduction in the quantity of the combustion auxiliary to be used and results in cutting the cost of production as well.

The exhaust steam is supplied through the steam line 179 and further through the steam line 185 to the acid purifying step 107, and also supplied through the steam line 179 and further through the steam line 187 to the esterifying step 109. The steam is utilized in a reboiler, a heater, and/or a vacuum generating device in each step.

Since the distillation of an organic acid or an organic acid ester is effected at a certain temperature under a vacuum, for example, the steam pertinent thereto is utilized for driving the vacuum generating device. Likewise, when an organic acid or an organic acid ester is distilled and purified, the distilling column such as a solvent separating column, a light-ends separating column, or a heavy-end separating column is furnished with a reboiler which serves the purpose of reboiling the bottom liquid of the distilling column. The steam pertinent thereto can be utilized as the heat transfer media for exchanging heat with the bottom liquid.

Further, when a distilling column such as a solvent separating column, a light-ends separating column, or a heavy-end separating column and a stripping column are used for distilling and purifying an organic acid or an organic acid ester, they are furnished with a heater which serves the purpose of heating the feed to be supplied thereto. The steam pertinent thereto can be used as the heat transfer media for the heater. Incidentally, the term "heater" as used herein may embrace such a preheater and a vaporizer.

When the organic acid or the organic acid ester happens to be an easily polymerizing substance, the use of a treated steam in the reboiler or the heater is particularly effective. When a steam of high pressure and high temperature generated as in the heat transfer media boiler 117 is used, it tends to induce polymerization of the acid or ester though it permits a decrease in size of the reboiler or the heater. The steam of high pressure, therefore, is dynamically recovered in the turbine 121 and converted therein to a steam of lowered pressure and lowered temperature. The steam discharged from the turbine 121 is utilized in the reboiler and the heater. The optional use of a regulating valve for further lowering the pressure and the temperature of the steam proves effective. The difference in temperature between the steam to be used in the reboiler and the heater and the easily polymerizing substance is properly not more than 50° C. and preferably not more than 30° C.

The pressure of the steam line 179 is as described above. The pressure of the steam line 185 and that of the steam line 187 do not need to be controlled equally throughout the entire lengths thereof. They may be controlled in ranges which are proper and necessary for the relevant lines branched to the target steam consuming devices. Otherwise, the control may be so effected as to retain the steam line wholly under an approximately equal pressure. In any event, when the steam is utilized as the heat transfer media for the reboiler and the heater, the pressure thereof is controlled generally in the range of 0.1–2 MPa gauge and preferably in the range of 0.1–0.6 MPa gauge. If the pressure of the line for supplying steam to the reboiler and the heater falls short of 0.1 MPa gauge, the shortage will be at a disadvantage in unduly decreasing the difference in temperature between the steam and the fluid being handled, impairing the thermal efficiency, and unduly enlarging the equipment. Conversely, if this pressure exceeds 1 MPa gauge, the excess will be at a disadvantage in readily inducing an easily polymerizing substance to polymerize.

As concrete examples of the reboiler to be used, a vertical reboiler, a horizontal reboiler, a kettle type reboiler, and a calandria type reboiler may be cited. The heaters which are usable herein include (1) a heating jacket disposed on the outer peripheral part of an esterifying reactor provided with a propeller type stirrer and adapted to introduce therein a heat transfer media for adjusting the temperature of the interior of the esterifying reactor and (2) a fixed shell-and-tube type heat exchanger adapted to supply the raw material as adjusted to the prescribed temperature to an esterifying reactor or a various column such as a distilling column or a stripping column, for example.

Further, when the steam is utilized for driving a vacuum generating device, the pressure of the steam line is controlled generally in the range of 0.3–2 MPa gauge and preferably in the range of 0.5–1 MPa gauge.

When the distillation is effected at the acid purifying step 107 and the esterifying step 109, it requires a condenser and a cooler. To the condenser and the cooler, a cooling water is circulated. Since this cooling water is used in a large quantity, it is generally circulated from a water cooling device by means of a large pump. The steam may be utilized as the power source for driving the pump. For this purpose, the steam of high pressure and high temperature from the heat transfer media boiler may be utilized. The surplus steam in the plant promises an effective service. By connecting an electric generator to a steam turbine prior to the discharge of the steam, this surplus steam is enabled to be converted into an electric energy and utilized as a power source.

Further, in the waste gas combustion device 113, the steam is generated by effectively utilizing the heat of combustion which is generated when the waste gas supplied from the absorbing step in the acid purifying step 107 through the line 165 is subjected to a treatment of combustion optionally after incorporation of a combustion auxiliary. It is permissible to treat in the same device the waste liquid emanating from the acid purifying step and the esterifying step and the waste gas emanating from the acid purifying step.

The steam which is generated in the waste gas combustion device 113 is forwarded from a steam line 171 to the steam line 179. The pressure of the steam generating device is so controlled as to equal to or to be 0.05–0.1 MPa higher than the pressure of the steam line to be connected.

The embodiment illustrated in FIG. 1 has been described above. From the viewpoint of simplifying the equipment, the individual steam lines may be used as one system as illustrated. Otherwise, a plurality of systems of steam lines (such as, for example, a steam line for high-pressure, a steam line for medium pressure, and a steam line for low-pressure) adapted to be controlled under pressures properly varied as occasion demands may be laid out. Specifically, the steams of different pressures obtained in the relevant steam generating devices may be supplied and used through the steam lines controlled to the different pressures so as to ensure supply of steams of pressures necessary for the relevant steam consuming devices. This layout is similarly adapted in FIG. 2 which will be specifically described herein below.

The process for the production of an organic acid and/or an organic acid ester and the steam system (partly expressed as "a step") which are used in another preferred embodiment of the method of this invention for the production of an organic acid and/or an organic acid ester, specifically in implementing a two-stage catalytic gas phase oxidation with one reactor, are schematically illustrated in FIG. 2. As a concrete example of the reactor, a reactor which has a shell partitioned with a shield into two chambers, i.e. a former-stage chamber for implementing the first-stage reaction of catalytic gas phase oxidation and a latter-stage chamber for implementing the second-stage reaction of catalytic gas phase oxidation, and has these chambers each adapted to permit circulation therein of a heat transfer media of a varying temperature. The reference numerals used in FIG. 2 are similar to those used in FIG. 1.

As regards the flow of the process for the production of an organic acid in the embodiment illustrated in FIG. 2, the raw material gas and an oxygen-containing gas (air and a recycled gas) are mixed at an elevated temperature and the resultant mixture is compressed by an oxygen-containing gas supplying device, supplied to the former-stage chamber of a reactor 201, and subjected therein to the first-stage reaction of catalytic gas phase oxidation. The gas formed by this reaction is then forwarded directly to the latter-stage chamber of the reactor 201 and subjected therein to the second-stage reaction of catalytic gas phase oxidation and consequently converted into an organic acid aimed at.

The reactor 201 used herein is a shell-and-tube type reactor. This reactor is enabled to effect a reaction of catalytic gas phase oxidation by supplying a raw material gas via a raw material supplying tube into a lot of reaction tubes (a tube bundle) disposed inside the shell of the reactor and packed with a relevant catalyst. At this time, the raw material gas formed by mixing the raw material for the reaction with a compressed preheated air which is an oxygen-containing gas is supplied, for example, through a raw material gas supply nozzle into a bundle of reaction tubes which are packed with, catalysts pertinent to the relevant chambers in the shell of the reactor, subjected to the catalytic gas phase oxidations pertinent to the chambers and consequently made to form respective reaction products, and then discharged collectively as a formed gas through a reaction gas discharge nozzle.

Thereafter, this formed gas is forwarded through a line 251, a waste heat boiler 203, and a line 253 to an acid purifying step 205 and subjected therein to a treatment which will be specifically described herein below and consequently made to form a purified organic acid. This purified organic acid is further forwarded through a line 255 to an esterifying step 207, subjected therein to a treatment which will be specifically described herein below and consequently made to form an organic acid ester, and withdrawn as the ester via a line 257. The esterifying step include a step for purifying the organic acid ester.

At an absorbing step in the acid purifying step 205, the formed gas which has passed the waste heat boiler 203 is led via the line 253 to an organic acid absorbing column and exposed therein to a solvent which is generally water and consequently collected as an organic acid solution. The organic acid solution thus obtained is forwarded to the acid purifying column.

In the acid purifying column, the water of the aqueous solution brought in from the absorbing step is expelled by distillation with an azeotropic solvent or extracted with a solvent to obtain the organic acid. Part of the water so separated is circulated through the interior of the system and the remainder thereof is purged as a waste water from the system. The organic acid-containing component obtained is then distilled to expel a light component and a heavy component and obtain a purified organic acid.

Then, at the esterifying step 207, the organic acid produced at the acid purifying step 205 is esterified by reaction with an alcohol. The reaction product of this esterification is subjected to a treatment of distillation and/or extraction and consequently separated into an unaltered organic acid, an alcohol, and an organic acid ester. Subsequently, the resultant product is distilled to expel the light component and the heavy component and obtain the purified organic acid ester.

The waste gas which occurs after the aqueous organic acid solution has been collected and separated at the absorbing step is forwarded through a line 261 to a waste gas combustion device 211, subjected therein to a treatment of combustion, and then purged as a waste gas out of the system via a line 267.

Then, part of the waste gas is forwarded through the line 261 and a line 262 to a gas heater 209, preheated therein to a prescribed temperature, subsequently supplied through a line 264 to a line 266, mixed therein with an oxygen-containing gas, then supplied to an oxygen-containing gas supplying device, properly compressed therein, and supplied through a line 259 to the reactor 201.

As the oxygen-containing gas supplying device, such a compressor 213 as depicted in FIG. 2 can be utilized. The oxygen-containing gas supplying device is preferred to be furnished with a steam turbine 219 which utilizes a superheated steam as the power source for the oxygen-containing gas supplying device as illustrated in FIG. 2. The oxygen-containing gas supplying device may be further furnished with a motor 221 as a component member of the device.

Incidentally, the aforementioned gas heater 209 may be similar to the gas heaters 111, 115 described in the embodiment illustrated in FIG. 1.

In the present embodiment, the process of production is provided with a steam system which serves the purpose of recovering and using the heat generated in the reaction of catalytic gas phase oxidation. This steam system recovers the generated heat in the form of steam and uses the recovered steam at the step for the reaction of catalytic gas phase oxidation and at the subsequent steps. Incidentally the generated heat is handled as explained in the embodiment of FIG. 1. The present embodiment may well be rated as a case of exalting the thermal efficiency of the entire steam system by enabling the plant to be stably operated and allowing effective recovery and utilization of the generated heat while leaving the heat without recovering the combustion of the waste liquid in the form of steam.

Now, the steam system in the present embodiment will be described below with reference to FIG. 2.

First, the heat transfer media which fill the shells of the former-stage and/or the latter-stage chamber is circulated as by a circulating pump through a line 269 to the heat transfer media boiler 213. In consequence of this circulation, the heat of reaction generated in the former-stage chamber of the reactor 201 is recovered in the form of steam through exchange of heat. The descriptions of the component devices, steam pressure, and pressure control means concerning the heat transfer media boiler 213 are similar to those of the heat transfer media boiler 117 already described in the embodiment of FIG. 1.

Part of the steam generated in the heat transfer media boiler 213 is forwarded though a steam line 273 to a super heater 215.

The pressure of the steam in the steam line 273 is controlled to equal to or to be 0.05–0.1 MPa lower than the pressure in the heat transfer media boiler. The control of the pressure of the steam line 273 is similar to that of the steam line 175 described in the embodiment of FIG. 1.

The steam brought in through the steam line 273 to the superheater 215 is superheated to produce a superheated steam by utilizing the heat of reaction in the former-stage and/or the latter-stage chamber of the reactor 201. Generally, the former-stage chamber is suitable for the production of the superheated steam because it has a higher temperature than the latter-stage chamber.

As the superheater, any of the shell-and-tube type heat exchangers in popular acceptance may be used.

Here, the pressure and the degree of superheating the steam in the superheater 215 are similar to the pressure and the degree of superheating the steam in the waste liquid treating device 119 described in the embodiment of FIG. 1.

The superheated steam which is generated in the superheater 215 is forwarded through a steam line 275 to the steam turbine 219 for use in the oxygen-containing gas supplying device. The thermal energy entrained by the superheated air of high temperature and high pressure is converted in the steam turbine into a useful dynamic energy (for mechanical work).

The description concerning the steam turbine 219 is similar to that of the steam turbine 121 in the embodiment of FIG. 1.

Part of the steam generated in the heat transfer media boiler 213 is forwarded through a steam line 283 branched from the steam line 273 to a steam line 277. The useful thermal energy entrained by this steam is also effectively utilized for complex applications and multiple-stage applications. Further, the steam generated in the waste heat boiler 203 and the steam generated in the waste gas combustion device 211 which will be specifically described herein below are similarly forwarded to a steam line 277. The useful thermal energy entrained by these steams is also effectively utilized in complex applications and multiple-stage applications.

Here, the pressure of the steam line 283 is controlled by means of a valve which utilizes the difference of pressure between the steam lines 273 and 277.

The exhaust steam which remains after the superheated steam has been used as a dynamic energy in the steam turbine 219, part of the steam generated in the heat transfer media boiler 213, and also the steam generated in the waste heat boiler 203 or the waste gas combustion device 211 are forwarded to the main steam line 277, forwarded therefrom through a steam line 279 to the gas heater 209, and used therein to heat the waste gas to a prescribed temperature through exchange of heat with the waste gas brought in from the acid purifying stem through the lines 261, 262.

Here, the description concerning the pressure of the steam line 277 and the purged steam from the system via the steam line 277 is similar to that concerning the steam line 179 described in the embodiment of FIG. 1.

The control of the pressure in the steam line 279 is also similar to that of the steam lines 191 and 193 depicted in FIG. 1.

The exhaust steam is forwarded from the steam line 277 through a line 280 to the steam line 205 and also from the steam line 277 through a steam line 281 to the esterifying step 207 and used in the reboiler, heater, and vacuum generating device in each of the relevant steps. The description of the steam consuming devices at the acid purifying step 205 and the esterifying step 207 and the pressures of the steam lines extended to these steam consuming devices is similar to the description of the steam consuming devices at the acid purifying step 107 and the esterifying step 109 and the pressures of the steam lines extended to the steam consuming devices in the embodiment of FIG. 1.

When the exhaust steam is forwarded through the steam line 277 and further through a steam line 278 to a waste liquid treating device 217 and used therein to treat the waste liquid for combustion, it is utilized in a waste liquid heating heat exchanger for elevating the temperature of the waste liquid. Specifically, this utilization is similar to the advantage of the secondary utilization of the steam through the steam line 183 described in the embodiment of FIG. 1.

In the waste liquid treating device 217, the waste liquid brought in from the acid purifying step 205 and the esterifying step 207 through a line 285 and a line 286 is subjected to a treatment of combustion optionally after incorporation therein of a combustion auxiliary for optimizing the efficiency of combustion. Incidentally, in the waste liquid treating device 217, the waste water and/or the waste oil emanating from the acid purifying step 205 and the waste water and/or the waste oil emanating from the esterifying step 207 may be treated either simultaneously or separately of each other in deference to such factors as the efficiency of combustion.

The waste liquid treating device 217 and the combustion temperature of the waste liquid are similar to the waste liquid treating device 119 and the combustion temperature of the waste liquid described in the embodiment of FIG. 1. Incidentally, the waste liquid treating device 217 may be utilized as a steam generating device similar to that depicted in FIG. 1, for example, besides being utilized as a steam consuming device as depicted in FIG. 2. The steam which is recovered in this device may be used as added as a superheated steam to the steam line 275 similarly to the pattern of FIG. 1. The pressure in the waste liquid treating device, the degree of superheating the steam, and the temperature of the heat recovered from the combustion gas involved herein are as described in the embodiment of FIG. 1.

Then, the formed gas obtained by the two-stage reaction of catalytic gas phase oxidation in the latter-stage chamber of the reactor 201 is forwarded through the line 251 to the waste heat boiler 203 and used therein to generate steam and recover residual heat by utilizing the generated heat entrained by the formed gas as the heat source for the waste heat boiler 203.

The temperature of the steam which is generated in the waste heat boiler 203, i.e. a steam generating device herein, is as described with respect to the waste heat boiler 105 in the embodiment of FIG. 1.

The steam generated in the waste heat boiler 203 is forwarded through a steam line 252 to the steam line 277.

Further, in the waste gas combustion device 211, the heat of combustion which is generated when part of the waste gas supplied from the line 261 through a line 263 is subjected to a treatment of combustion optionally after incorporation therein of a combustion auxiliary is effectively utilized to generate steam.

The steam generated in the waste gas combustion device 211 is forwarded through a steam line 265 to the steam line 277. The pressure of the steam generating device is generally controlled to equal to or to be 0.05–0.1 MPa higher than the pressure in the steam line to be connected.

Incidentally, the steam may be either purged from the system or condensed in a heat exchanger and utilized as a condensate for supply to a boiler, for example.

The organic acid to which the method of this invention can be applied may be any of the organic acids that can be produced at all by the reaction of catalytic gas phase oxidation. These organic acids include (meth)acrylic acid, phthalic acid, and maleic acid, for example, preferably (meth)acrylic acid. The method of production according to this invention may embrace a step for further esterifying the organic acid and producing an organic acid ester. As concrete examples of the organic acid ester, esters of (meth)acrylic acid such as methyl (meth)acrylate, ethyl (meth)acrylate, n-butyl (meth)acrylate, hydroxypropyl (meth)acrylate, and 2-ethylhexyl (meth)acrylate may be cited.

Incidentally, the method for producing an organic acid and/or an organic acid ester as contemplated by this invention does not need to be limited to the typical embodiment illustrated in FIG. 1 and FIG. 2 but may be implemented by suitably combining or recombining the embodiment illustrated in FIG. 1 and FIG. 2 without departure from the technical scope of this invention.

EXAMPLES

Example 1

By using the mode of FIG. 1, methyl methacrylate was produced via methacrylic acid. To the first-stage reactor 101, isobutylene as the raw material, an oxygen-containing gas, and steam were supplied. As the heat transfer media for use in the reactor, a mixture of 50 mass % each of potassium nitrate and sodium nitrite was used. The heat transfer media of the reactors 101, 103 were mixed and the resultant mixture was supplied to the heat transfer media boiler 117 and made therein to generate high-pressure steam and the generated steam was subsequently circulated to the reactors. The heat transfer media boiler was controlled under a pressure of 4.1 MPa gauge and the steam generated at 21.2 T/h was discharged into a steam line controlled under a pressure of 4.0 MPa gauge (high-pressure steam) within the plant. The reaction gas was cooled in the waste heat boiler 105 to 260° C. and introduced into an absorbing column in the acid purifying step 107. From the waste heat boiler 105, the steam was discharged into the steam line controlled under a pressure of 4.1 MPa gauge (high-pressure steam). The high-pressure steam was consumed at a rate of 3.5 T/h as in the gas heaters 111, 115 which were users of high-pressure steam and the remainder thereof, 19.9 T/h, was forwarded to the waste liquid treating device. The waste gas emanating from the absorbing column was subjected to combustion with a catalyst at the waste gas treating step 113 and the heat of combustion was recovered in the form of steam. The steam recovering device was controlled under a pressure of 0.25 MPa gauge. The steam generated at a rate of 2.8 T/h was discharged into the steam line controlled under a pressure of 0.2 MPa gauge (low-pressure steam) in the plant. Part of the gas which remained after the recovery of heat was heated and recycled to the second-stage reactor 103 and the remainder of the gas was purged out of the system. The liquid collected in the bottom of the absorbing column was extracted, distilled, and purified in the acid purifying step to obtain methacrylic acid. The methacrylic acid was further esterified with methanol at the esterifying step 109, and distilled and purified to afford methyl methacrylate. At the purifying steps for the acid and the ester, the steam was used in a thermosiphon reboiler, a heater, and a vacuum generating device (steam ejector). The steam, inclusive of the steams introduced under a pressure of 0.6 MPa gauge (medium-pressure steam) and a pressure of 0.2 MPa gauge (low-pressure steam) into the reactor, was consumed at a rate of 17.3 T/h. The waste liquid which occurred in the acid purifying step and the esterifying step was treated in the waste liquid treating device. The waste water partially vaporized in the vaporized by using a low-pressure steam at a rate of 4.2 T/h. The waste water steam, the waste water, the waste oil, and the combustion auxiliary were treated by combustion in the furnace at a temperature of 980° C. The combustion gas was subjected to recovery of heat up to 230° C. The gas resulting from the recovery of heat and the steam from the reaction system were together used to generate superheated steam under a pressure of 4 MPa gauge at a temperature of 350° C. at a rate of 24.3 T/h. The superheated steam was wholly used in the air compressor and the back-pressure turbine for the recycled gas compressor and recovered in steam lines controlled under pressures of 0.6 MPa gauge and 0.2 MPa gauge. The surplus steam was discharged as a low-pressure steam at a rate of 5.6 T/h. Consequently, the steam generating system and the steam consuming system could be stably operated. Further, by driving the compressor with a turbine, the power consumption was allowed a saving of about 1600 kW.

Example 2

Acrylic acid was produced by using the mode of FIG. 2. To the reactor 201, propylene as the raw material and an oxygen-containing gas were supplied. As the heat transfer media for use in the reactor, a mixture of 50 mass % each of potassium nitrate and sodium nitride was used. There actor was partitioned with a shield and the heat transfer media used in the separated chambers were mixed and the resultant mixture was supplied to the heat transfer media boiler 213 and used therein to generate high-pressure steam, and this steam is then circulated to the reactor. The heat transfer media boiler 213 was controlled under a pressure of 2.1 MPa gauge and the steam consequently generated at a rate of 14.3 T/h was forwarded to a high-pressure steam line controlled under a pressure of 2.0 MPa gauge and further heated in the superheater 215 up to 270° C. The superheated steam consequently formed was used in the back-pressure turbine used in the oxygen-containing gas compressor. The treated steam was discharged into a steam line controlled under a pressure of 0.6 MPa gauge (medium-pressure steam) in the plant. The reaction gas was cooled in the waste heat boiler to 170° C. and introduced into the absorbing column in the acid purifying step 205. The waste heat boiler was controlled under a pressure of 0.25 MPa gauge and the steam generated at a rate of 1.2 T/h was discharged into the steam line controlled under a pressure of 0.2 MPa gauge (low-pressure steam) in the plant. The waste gas emanating from the absorbing column was partly recovered as a recycled gas via the oxygen-containing gas compressor to the reactor 201. The remainder of the waste gas was subjected to combustion with a catalyst in the waste gas combustion device. The heat of combustion of the waste gas was recovered in the form of steam at a rate of 2.1 T/h. Incidentally, the steam recovering device was controlled under a pressure of 0.65 MPa gauge and the steam consequently recovered was discharged into the steam line controlled under a pressure of 0.6 MPa gauge (medium-pressure steam) in the plant. The liquid collected in the bottom of the absorbing column was distilled and purified at the acid purifying step to afford acrylic acid. At the acid purifying step, the steam was used in a thermosiphon reboiler, a heater, and a vacuum generating device (steam ejector). The steams used under pressures of 0.6 MPa gauge (medium-pressure steam) and 0.2 MPa gauge (low-pressure steam) were collectively consumed at a rate of 8.6 T/h. The waste liquid which occurred at the acid purifying step was disposed of by the waste liquid treating device. The waste water was partially stripped with the air for combustion in a stripping column. The waste water steam, the waste water, the waste oil, and the combustion auxiliary were disposed of by combustion in the submerged combustion furnace at a temperature of 920° C. Incidentally, the waste water to be supplied to the stripping column was preheated with the combustion gas and the low-pressure steam at a rate of 0.4 T/h. The surplus steam occurring at a rate of about 8.6 T/h in the acrylic acid plant was discharged into the esterifying step 207. As a result, the steam generating system and the steam consuming system could be stably operated. By Driving the compressor with a turbine, the power consumption was allowed a saving of about 520 kW.

The entire disclosure of Japanese Patent Application No. 2001-266189 filed on Sep. 3, 2001 including application, claims, drawings and summary are incorporated herein by reference in its entirety.

What is claimed is:

1. A method for the production of an organic acid and/or an organic acid ester, wherein heat generated in a process for producing an organic acid and/or an organic acid ester by using a catalytic gas phase oxidation is recovered in the form of steam, said generated heat contains at least heat generated in said catalytic gas phase oxidation and heat generated when waste liquid formed by said catalytic gas phase oxidation is treated, by combustion and said steam is used in a form selected from the group consisting of:

(1) thermal energy, (2) dynamic energy, and (3) electrical energy in said process for producing an organic acid and/or an organic acid ester.

2. A method according to claim 1, wherein said waste liquid is a waste liquid at an acid purifying step and/or an esterifying step.

3. A method according to claim 1, wherein said catalytic gas phase oxidation is a multiple-stage catalytic gas phase oxidation and one heat transfer media boiler recovers heat generated at each stage.

4. A method according to claim 3, wherein said catalytic gas phase oxidation is carried out by using two or more reactors differing in reaction temperature.

5. A method according to claim 3, wherein said catalytic gas phase oxidation is carried out by using a reactor furnished with two or more chambers differing in reaction temperature.

6. A method according to claim 1, wherein said pressure of the generated steam is controlled in a steam generating device and in a steam line.

7. A method according to claim 6, wherein said pressure of the generated steam is controlled by the use of a valve.

8. A method according to claim 1, wherein said generated steam is used for a function selected from the group consisting of:
(1) a heat exchanger for heating a gas supplied to a reactor for the catalytic gas phase oxidation,
(2) a power source for a device supplying an oxygen-containing gas to a reactor for the catalytic gas phase oxidation,
(3) a steam applied for the catalytic gas phase oxidation,
(4) a reboiler, a heater, or a vacuum generating device at an organic acid purifying step and/or an esterifying step,
(5) a heater for waste water, and
(6) a power source for a pump to be used at an organic acid purifying step and/or an esterifying step.

9. A method according to claim 1, wherein the organic acid is (meth)acrylic acid.

* * * * *